(12) United States Patent
Bhogal et al.

(10) Patent No.: US 12,029,441 B2
(45) Date of Patent: Jul. 9, 2024

(54) THROMBECTOMY DEVICE

(71) Applicant: Phenox GmbH, Bochum (DE)

(72) Inventors: Pervinder Bhogal, London (GB); Hans Henkes, Stuttgart (DE); Hermann Monstadt, Bochum (DE); Ralf Hannes, Dortmund (DE)

(73) Assignee: Phenox GmbH, Bochum (DE)

( * ) Notice: Subject to any disclaimer, the term of this patent is extended or adjusted under 35 U.S.C. 154(b) by 969 days.

(21) Appl. No.: 16/979,849

(22) PCT Filed: Mar. 6, 2019

(86) PCT No.: PCT/EP2019/055543
§ 371 (c)(1),
(2) Date: Sep. 10, 2020

(87) PCT Pub. No.: WO2019/174988
PCT Pub. Date: Sep. 19, 2019

(65) Prior Publication Data
US 2021/0161545 A1   Jun. 3, 2021

(30) Foreign Application Priority Data
Mar. 12, 2018 (DE) .......................... 102018105671.0

(51) Int. Cl.
*A61B 17/221* (2006.01)
*A61M 25/00* (2006.01)
(Continued)

(52) U.S. Cl.
CPC ....... *A61B 17/221* (2013.01); *A61M 25/0021* (2013.01); *A61B 2017/00526* (2013.01);
(Continued)

(58) Field of Classification Search
CPC ........ A61B 17/221; A61B 2017/00526; A61B 2017/2215; A61B 2090/3966;
(Continued)

(56) References Cited

U.S. PATENT DOCUMENTS

| 5,171,233 A | 12/1992 | Amplatz et al. |
| 6,245,089 B1 | 6/2001 | Daniel et al. |

(Continued)

FOREIGN PATENT DOCUMENTS

| DE | 2806030 | 8/1979 |
| EP | 2926747 | 10/2015 |

(Continued)

OTHER PUBLICATIONS

International Search Report from International Application No. PCT/EP2019/055543 dated Aug. 12, 2019.
Mayer, et al., Stroke, American Heart Association, 2232 (2002).

*Primary Examiner* — Katherine M Rodjom
(74) *Attorney, Agent, or Firm* — Crockett & Crockett, PC; K. David Crocket, Esq.; Niky Economy Syrengelas, Esq.

(57) ABSTRACT

A device (1) for removing thrombi from blood vessels, wherein the device (1) has an expanded state in which it is set free temporarily in the blood vessel and a compressed state in which it is introduced into and removed from the blood vessel through a microcatheter, wherein the device (1) has a proximal (2), a middle (3) and a distal portion (4), with the middle portion (3) having a substantially cylindrical structure and the proximal portion (2) being coupled to an insertion aid (5), and the distal portion (4) having a substantially cylindrical basic structure, with a constriction (6) being arranged between the middle (3) and distal portion (4), and the distal portion (4) being at least partially covered by a membrane (7). The inventive device (1) is characterized by (Continued)

the fact that thrombus fragments becoming detached from the thrombus to be captured are safely retained and removed from the blood vessel.

12 Claims, 8 Drawing Sheets

(51) Int. Cl.
  *A61B 17/00* (2006.01)
  *A61B 90/00* (2016.01)
(52) U.S. Cl.
  CPC .............. *A61B 2017/2215* (2013.01); *A61B 2090/3966* (2016.02); *A61M 2025/0042* (2013.01)
(58) Field of Classification Search
  CPC ....... A61M 25/0021; A61M 2025/0042; A61F 2/01; A61F 2/0105; A61F 2/012; A61F 2/013; A61F 2/014; A61F 2002/016
  See application file for complete search history.

(56) References Cited

U.S. PATENT DOCUMENTS

| | | | |
|---|---|---|---|
| 2010/0087850 A1 | 4/2010 | Razack | |
| 2011/0184456 A1* | 7/2011 | Grandfield | A61B 17/320725 606/200 |
| 2012/0265238 A1* | 10/2012 | Hopkins | A61F 2/0105 606/200 |
| 2014/0046359 A1 | 2/2014 | Bowman et al. | |
| 2014/0121672 A1* | 5/2014 | Folk | A61F 2/013 606/127 |
| 2015/0374483 A1 | 12/2015 | Janardhan | |
| 2016/0192956 A1* | 7/2016 | Brady | A61F 2/013 606/159 |
| 2017/0181835 A1* | 6/2017 | Kleshinski | A61F 2/013 |
| 2017/0189041 A1 | 7/2017 | Cox et al. | |

FOREIGN PATENT DOCUMENTS

| | | |
|---|---|---|
| WO | WO2008049386 | 3/2008 |
| WO | WO2009132859 | 11/2009 |
| WO | WO2012156069 | 11/2012 |

\* cited by examiner

THROMBECTOMY DEVICE

FIELD OF THE INVENTIONS

The invention relates to a device for removing thrombi from blood vessels, with the device being provided in an expanded state in which it is liberated in the blood vessel and in a compressed state in which it is introduced into and removed from the blood vessel through a microcatheter, wherein the device having a proximal, a middle and a distal portion, the middle portion having a substantially cylindrical structure and the proximal portion being coupled to an insertion aid.

BACKGROUND

Thromboembolic diseases such as myocardial infarction, pulmonary embolism, peripheral thrombosis, organ embolism, etc. are typically caused by a thromboembolus (hereinafter referred to as thrombus or clot), i.e. a viscoelastic blood clot consisting of blood platelets, fibrinogen, coagulation factors, etc., which has become lodged in a blood vessel and completely or partially occludes it. The obstruction of organ arteries also leads to the supply of oxygen and nutrients to the associated tissue being interrupted. The disorder of the functional metabolism linked with functional losses is closely followed by a failure of the structural metabolism resulting in the relevant tissue becoming destroyed (infarction). Organs most frequently affected in this way are the heart and the brain. However, such changes also affect the arteries of the extremities and the pulmonary arteries. Moreover, venous thromboses and thromboembolic occlusions are frequently occurring in the leg and pelvic veins. The disease pattern of a thrombotic occlusion of an intracranial sinus may lead to severe intracerebral hemorrhage due to an impairment of venous drainage of brain tissue.

In view of the severity of the disease patterns associated with thromboembolism and the prevalence rate of such diseases various techniques have been developed aimed at dissolving or removing thrombi.

It is known in this context to treat such patients with thrombolytic agents such as streptokinase or urokinase or anticoagulants which serve the purpose of thrombolysis or the inhibition of the clot growth. Since these treatment methods are usually time-consuming, they are often combined with methods that serve to reduce the size of or remove the thrombus or embolus.

Aside from open surgical operations prior art techniques more and more embrace the use of transluminal or endovascular, catheter-guided interventional therapy methods because these are of less invasive nature. It is thus known to remove the clot from the patient's body by means of vacuum producing suction catheters or mechanically using catheters provided with capturing cages, coils, hooks or similar elements; refer to U.S. Pat. No. 6,245,089 B1, U.S. Pat. No. 5,171,233 A1, Thomas E. Mayer et al., Stroke 2002 (9), 2232.

Drawbacks associated with thrombolytic treatment methods are that they seldom bring success after relevant time frame requirements have expired. Also, the known transluminal devices often fail to entirely remove the clot and, moreover, there is a risk of the clot or fragments thereof being released into the blood stream thus passing on to vessels of smaller lumen where they may only be reached or treated with difficulty.

Disclosed in WO 2012/156069 A1, a thrombectomy device is known comprising a slit that extends helically over the outer surface of the device, with a clamping bracket covering the slit at the proximal end in a wave-like manner. When the thrombus has been captured, the device is withdrawn into a microcatheter (aspiration catheter) and removed from the blood vessel system together with the thrombus. This thrombectomy device is particularly suitable for the removal of thrombi from small-lumen or highly tortuous vessels such as those of the brain.

Basically, the thrombectomy devices known in the state of the art have proven themselves, but the problem may nevertheless arise that due to the constant flow of blood the thrombus detaches from the device again after it has been caught with the aid of the device. Particularly with less solid thrombi, there is a risk that parts of the thrombus are released. Parts of the thrombus released in this way may reach other areas of the blood vessel system where they may possibly cause an (ischemic) stroke.

It is, therefore, the objective of the present invention to provide a device for the removal of thrombi by means of which the thrombus can be captured and eliminated from the blood vessel system, but said device also preventing the thrombus or thrombus fragments from becoming detached from the device.

SUMMARY

In accordance with the invention, this objective is achieved by providing a device for removing thrombi from blood vessels, with the device being provided in an expanded state in which it is set free in the blood vessel and in a compressed state in which it is introduced into and removed from the blood vessel through a microcatheter, wherein the device having a proximal, a middle and a distal portion, with the middle portion having a substantially cylindrical structure and the proximal portion being coupled to an insertion aid, with the distal portion having a substantially cylindrical basic structure and there is a constriction between the middle and distal portions, and the distal portion being at least partially covered by a membrane.

Thrombectomy devices provided in the distal area with a polymer skin intended for capturing thrombus fragments are already known from the state of the art; however, in these devices the membrane is stretched and positioned in such a way that thrombus fragments are caught by the polymer skin within the device. Due to the fact that the polymer skin is virtually impermeable to the blood, problems are encountered when retracting the device into the microcatheter to finally eliminate the thrombus. The invention is based on the fact that any thrombus fragments that may occur are intercepted outside the actual device, namely in the area of the constriction, whereby the membrane stretched out and positioned in the distal section ensures by means of its outer surface that the thrombus fragments are prevented from entering more distally located areas of the blood vessel system. When the device is drawn back into the microcatheter, the thrombus fragments captured within the constriction zone are thus retracted along the inner wall of the vessel until they are finally drawn into and accommodated in the microcatheter upon withdrawal of the device. It should be noted in this respect that the microcatheter accommodating the device and the thrombus are usually so-called aspiration catheters, which at the same time exert a certain suction effect that additionally ensures that the thrombus and trapped thrombus fragments enter the aspiration catheter.

In this embodiment, the membrane essentially has a funnel shape, with the thin end of the funnel pointing towards the constriction and the wide end pointing in distal direction. Over its circumference, the membrane is in contact with the inner wall of the vessel and is capable of collecting thrombus fragments or abrasion. In the context of the invention, the term constriction shall be understood to mean that the diameter of the device in the area of the constriction is significantly smaller than both the diameter of the middle section and the diameter of the distal section. Preferably, the diameter in the area of the constriction amounts to ≤80% of the diameter in the distal and middle section, preferably is ≤70%, more preferably ≤60%, in particular amounts to approx. 50%.

With the help of a microcatheter, the device is navigated to the location in the blood vessel system where it is put to use for thrombus removal. Here the device is released in the area of the thrombus to enclose it. Usually, the release/liberation takes place in the thrombus itself or distal to the thrombus. Such a release is achieved via the insertion aid to advance the device in the distal direction or retracting the microcatheter in the proximal direction while simultaneously securing the device by means of the insertion aid. By release it is understood that the device is moved out of the microcatheter so that its expansion can take place. As the device is not designed to remain permanently in the blood vessel, the device usually remains connected to the insertion aid. The insertion aid is usually an insertion wire. When released, the device assumes an expanded state in which it adapts to the vessel lumen and makes contact with the inner wall of the vessel. As a rule, the expanded state forms a secondary structure previously impressed on the device. In particular, this applies if the device is entirely or partially made of a shape memory material, especially a shape memory metal. The impression of a secondary structure is typically achieved by heat treatment.

The thrombus is captured by the device, either when expansion of the device takes place and/or during retraction. As soon as the thrombus is located inside the device or the device has partially penetrated the thrombus, the device is retracted in the direction of the micro(aspiration)-catheter. Retraction is achieved by moving the insertion aid in the proximal direction. Since the insertion aid is coupled to the proximal section of the device, the proximal section of the device also moves towards the catheter ultimately causing the device as well as the thrombus to be entirely accommodated in the catheter. Fragments of the clot still adhering to the wall of the vessel are removed and entrained by the shearing action of the struts. The thrombus is thus drawn into the catheter and removed from the body together with the catheter.

As already mentioned above, a certain amount of suction is usually exerted in the direction of the catheter in order to additionally ensure that any clot fragments that may have come loose are also drawn in.

The terms "proximal" and "distal" are to be understood such that they refer as proximal to parts that point towards the attending physician when inserting the device, and as distal to parts that point away from the attending physician. Typically, the device is thus moved forward in distal direction with the aid of a microcatheter. The term "axial" refers to the longitudinal axis of the device extending from proximal to distal while the term "radial" denotes levels/planes extending vertically thereto.

Preferably, at least the middle section of the device has a large number of open cells distributed over its outer surface. In other words, a lattice or mesh structure is thus formed that is made up of struts or braces, so that the basic cylindrical structure features a large number of openings or meshes on the outer surface. The size of the open cells is dimensioned in such a way that, on the one hand, a captured thrombus cannot pass through the cells but is securely retained by the device and, on the other hand, the flow of blood is ensured. Moreover, the mesh structure is built up in such a way that the struts when released are penetrating or even completely cut through a thrombus in order to hold it in place.

Aside from the middle section, the proximal and/or distal section may also have a similar structure comprising open cells distributed on the outer surface. In this respect, the structure or design of the proximal, middle and distal sections may not differ significantly, apart from the fact that the distal section is separated from the middle section by a constriction and at least partially covered by a membrane, while the proximal section generally tapers off and thus reduces its diameter in the direction of the insertion aid/insertion wire.

The term "open cell" refers to the lattice structure, regardless of whether the cell is separated from the environment by a membrane, meaning, even a cell that is covered by a membrane is referred to as an open cell. A membrane cover shall be understood as any covering of a structure, regardless of whether the membrane is applied to the outside or to the inside of the lattice structure or whether the lattice structure is embedded in a membrane.

The lattice structure of the device, or at least of the middle section, may be a braided structure, that is, may consist of individual wires or wire bundles forming struts which are braided together and at the points of intersection of the wires/wire bundles extend above and below each other. A cut structure is preferred, however, in which the lattice structure is cut out of a tube of suitable diameter by means of a laser. The material is usually a metal, however plastic material may be employed as well. The material must have sufficient elasticity to allow contraction to the diameter of a customary catheter and, moreover, bring about the expansion to the desired diameter when liberated from the catheter. Moreover, it is expedient to electropolish the lattice structure to make it smoother and more rounded and thus render it less traumatic. This also reduces the risk of germs or other impurities adhering to the structure. The struts or wires may have a round, oval, square, rectangular or trapezoidal cross section, with the edges being advantageously rounded off in the event of a square, rectangular or trapezoidal cross section. Flat webs/wires in the form of thin strips, especially metal strips can be employed as well. In case rectangular and trapezoidal embodiments are provided, it is preferable for the narrow side of the cross-section to face the vessel wall, which facilitates the penetration of the thrombus into the mesh structure.

Apart from iron alloys (stainless steel, spring steel) and cobalt-chromium alloys especially shape-memory alloys are suited for use, for example binary nickel-titanium alloys (nitinol) and ternary nickel-titanium-chromium alloys (chromium-doped alloys). Nitinol in particular is known for application in self-expanding structures in the neurovascular field.

The device proposed by the invention can initially be manufactured as a flat structure which is then rolled into a cylindrical structure. The device may be provided with a slit extending in the longitudinal direction of the device over the outer surface of at least part of the device. For example, the slit can run parallel to the longitudinal axis of the device or extend in a spiral or helix configuration over the outer surface. In the latter case, said slit may extend to form a complete coil/helix of 360° but may also be arranged to just form a partial coil/helix for example of 180° or 120°. A helical configuration of the slit offers an additional advantage in that the edges of the device along the slit move tangentially along the circumference of the vessel wall when pulled which improves the shearing effect. Moreover, the helical or coiled extension of the slit also improves (reduces) the bending stiffness in such a way that better adaptation to tortuous vessel patterns is possible. This not only facilitates placement of the device but also the extraction of clots from complex vessel structures. The outer surface of the device is open in the area of said slit with the width of the slit at the place of application also being determined by the lumen of the vessel since the device when released from the catheter is capable of unfolding only to such an extent as permitted by the vessel lumen.

The slit may extend over the entire length of the device, but it is preferable that the slit only extends over part of the device length. In the proximal section of the device, a clip may be arranged, for example, to extend over the slit, as described in WO 2012/156069 A1. This clip increases the radial force of the self-expanding structure and, moreover, serves to secure the oppositely arranged edges of the device alongside the slit in position relative to each other.

The number of open cells that are arranged adjacent to each other on the outer surface orthogonally to the longitudinal axis of the device is at least 2, but preferably 3 to 5. Adjacent cells are those cells that would lie next to each other orthogonal to the longitudinal axis of the device if the structure were cut open and spread flat. The correct selection of open cells depends, among other things, on the size of the blood vessel in which the device is to be put to use. As a rule, the larger the diameter of the blood vessel, the larger the number of adjacent cells arranged side by side, because in the expanded state the device must cover a larger total circumferential area. Aside from this, the general rule is that a lower number of open cells results in a more flexible device, which can be of advantage when the device has to be navigated inside tightly tortuous blood vessels. On the other hand, with the outer surface area being identical a fewer number of openings also implies that the size of the openings increases. The size of the openings should be selected to prevent, to the extent possible, the thrombus or thrombus fragments from escaping through the openings. In general, it has proven to be a good practice to use devices in which the number of open cells arranged adjacent to each other along the circumference on the outer surface orthogonal to the longitudinal axis of the device amounts to between 3 and 5.

It has been found to be useful if the membrane arranged in the distal section of the device has at least one opening which is preferably located centrally. If the membrane has a funnel shape in its entirety, the opening is thus located at the thin end of the funnel in the middle. The opening ensures that even if a membrane is used that is largely impermeable to liquid, the flow of blood through the device is ensured, thus reducing the risk of ischemia. Furthermore, the opening also facilitates the retraction of the device towards the catheter because it prevents blood congestion.

The constriction arranged between the middle and distal section is preferably produced by means of a heat treatment. In other words, the device is initially produced with its normal cylindrical structure, following which a heat treatment is carried out to create a constriction, said constriction constituting an essential characteristic of the described embodiment of the invention. For this purpose, the device is exposed to heat to create a condition under which the device can be transformed particularly well to produce a constriction, especially when shape memory materials such as nitinol are used.

According to an alternative embodiment which is to be considered independently of the embodiment elucidated hereinbefore, the invention relates to a device for removing thrombi from blood vessels, said device being provided in an expanded state in which it is released in the blood vessel and in a compressed state in which it is introduced into and removed from the blood vessel through a microcatheter, said device having a proximal, a middle and a distal portion, with at least the middle and distal portions having a substantially cylindrical structure of struts forming a plurality of open cells distributed over the outer surface of the device, and the proximal portion being coupled to an insertion aid, wherein the struts are bent inwardly at the distal end of the distal portion, and the distal portion is at least partially covered by a membrane.

As per this alternative embodiment, thrombi becoming detached from the device or thrombus fragments that come loose from the thrombus are collected by the distal end of the device, which is covered by a membrane. It is of prime importance in this respect that the struts located at the distal end of the distal section are bent inwards and the distal end is rounded overall. In this way, the distal end forms a bulging shape that comprises open cells or meshes. The distal end thus becomes significantly more atraumatic resulting in the risk of damaging the vessel walls to be reduced. What is more, the fact that the struts are bent inwards at the distal end results in the membrane to be securely held in place and not to be stretched excessively at any point, as this would increase the risk of the membrane rupturing. Because the struts are bent inwards, i.e. in the direction of the device's longitudinal axis extending centrally through the device, the distal end of the device has an overall rounded shape and can thus be easily navigated within the blood vessel.

Due to the fact that in this second embodiment of the invention the membrane generally has no opening, the membrane should at least be partially permeable to liquids, in particular blood in this case. In this way, it is ensured that the overall flow of blood through the blood vessel is maintained. Aside from this, retraction of the device into the catheter is facilitated when blood is allowed to pass through the membrane from one side of the membrane to the other, distal side.

The permeability of the membrane can be adjusted as necessary to achieve a more or less effective filtering effect. On the one hand, regarding the flow of blood high permeability will be beneficial, whereas low permeability is advantageous, on the other hand, to make sure even small thrombus fragments are intercepted.

Similarly to the first embodiment, it is also useful for the second embodiment if the number of open cells positioned next to each other on the outer surface orthogonal to the longitudinal axis of the device amounts to at least 2, preferably ranges between 3 and 5. As regards the criteria governing the selection of the optimum number of open cells, the remarks made above for the first embodiment shall likewise apply.

As a general rule, the statements made in connection with the first embodiment of the invention apply in the same way to the second embodiment, unless the design of the device or the context indicates or requires otherwise. In particular, the remarks stated with respect to the lattice/mesh structure, the construction comprising individual open cells, the materials used or the provision of a slit through the device as well as the handling of the device also apply to the second embodiment.

Bending of the struts at the distal end of the distal section is preferably achieved by heat treatment. In other words, the device is initially produced with its normal cylindrical structure, following which a heat treatment is carried out to exert a specific influence on the configuration of the struts at the distal end. For this purpose, the device is exposed to heat to create a condition under which the device can be transformed particularly well to achieve a rounding of the distal end, especially when shape memory materials such as nitinol are used.

It applies to both embodiments of the invention that the insertion aid is preferably an insertion wire, as it is sufficiently well known in the state of the art. The insertion aid may be coupled to the proximal portion of the device at one or more attachment points. Typically, the struts of the device converge in the proximal section towards the insertion aid. It is expedient here, if the coupling point(s) is (are) arranged shifted in the direction of the outer surface in relation to the centrally extending longitudinal axis of the device, i.e. located radially outward. Such an eccentric arrangement of the coupling or attachment point offers advantages in that the flow of blood is disturbed as little as possible. Upon release of the device from the microcatheter, the coupling point may thus be located in contact with the vessel wall.

Meaningfully, the device is provided with one or several radiopaque markers allowing the attending physician to visualize it. The radiopaque markers may, for example, consist of platinum, palladium, platinum-iridium, tantalum, gold, tungsten or other metals opaque to radiation. They allow the attending physician to see whether the device is correctly positioned relative to the thrombus to be removed and make corrections if necessary. It is also conceivable to provide at least some areas of the device with a coating of a radiopaque material, for example with a gold coating. This coating can, for example, have a thickness of between 1 and 6 µm. The coating with a radiopaque material need not be applied to the entire device. However, even if a radiopaque coating is provided, it may be useful to arrange one or more additional radiopaque markers. Another possibility is to sheathe individual struts with a helix or wire consisting of a radiopaque material such as platinum.

Especially for the second embodiment of the invention, it is seen expedient to provide radiopaque markers in the area of the proximal end of the membrane covering, that is, where, as viewed from the proximal end, the membrane covering begins. When retracting the device into an aspiration catheter, the treating physician can determine from the position of the radiopaque markers when the proximal end of the covering reaches the distal inlet of the aspiration catheter. It may be advisable not to withdraw the device further into the aspiration catheter to avoid trapped thrombus fragments from being "squeezed out", and instead to move the aspiration catheter with the device not fully retracted back proximally and then remove it from the blood vessel system.

Where the device is covered by a membrane, it may be attached to the lattice structure on the inside or on the outside. However, the lattice structure is preferably embedded in the membrane. This can be achieved by first presenting a lattice structure, around which fibers are subsequently spun or braided in such a way that a membrane with an embedded lattice structure is created. Relevant processes are sufficiently known from the state of the art, for example the so-called electrospinning method.

It is also possible to initially provide a mandrel onto which a 1st membrane is applied. Following this, the lattice structure itself is applied to the 1st membrane before a 2nd membrane is finally applied. In this way, the individual struts that make up the device are enclosed by membranes. In areas of the device where a membrane must not necessarily be arranged or is undesirable, it can still be removed afterwards.

As far as a membrane is referred to within the scope of the invention, it shall be clearly understood that this can also mean more than one membrane. It may therefore be a continuous membrane covering larger areas of the device, but it is also conceivable to provide several individual membranes to cover certain areas of the device. These individual membranes may be located adjacent to each other to form a uniform surface, but it is also possible for gaps to exist between the membranes as long as the objective associated with the device, which is to capture thrombus fragments, is warranted. A membrane may consist of several layers. In the event several membranes or membrane layers are arranged on top of each other, this arrangement shall also be understood as a membrane in the sense of the invention.

In the preferably employed electrospinning process, fibrils or fibers are separated from a polymer solution and deposited on a substrate by applying an electric current. Said deposition causes the fibrils to agglutinate into a non-woven fabric. As a rule, the fibrils have a diameter ranging between 100 and 3,000 nm. Membranes obtained by electrospinning have a very uniform structure. The membrane is tenacious, withstands mechanical stresses, and can be pierced through mechanically without the resulting opening giving rise to cracks propagating from it. The thickness of the fibrils as well as the degree of porosity can be controlled by selecting process parameters as appropriate. In the context of producing the membrane and with respect to materials suitable for this purpose, special attention is drawn to publications WO 2008/049386 A1, DE 28 06 030 A1 and literature referred to therein.

Instead of using electrospinning, the membrane may also be produced by an immersion or spraying process such as 'spray coating'.

The membrane can be manufactured of polymer material such as polytetrafluoroethylene, polyester, polyamides, polyurethanes or polyolefins. Especially preferred are polycarbonate urethanes (PCU), which can be applied, for example, in a solvent such as chloroform. An integral connection of the membrane with the lattice structure is particularly desirable. The adhesion of the membrane to the struts forming the lattice structure can be further improved by silanizing the struts.

Coupling points may be simple weld points where the inserting aid/insertion wire and the proximal portion of the device are brought together. Also conceivable are customary coupling elements via which the device can be detached. Although it is normally not intended that the device proposed by the invention remains at the placement site, unlike for example stents, this may in exceptional cases be necessary if a retrieval is not indicated for medical reasons, for example because it would cause harm to the patient. In such a case, the device can remain in the body similar to a stent and be effectively put to use in that it forms out a duct or channel within the clot, and the mesh structure thus causes the clot to be pressed against the vessel wall, with the flow of blood being maintained due to the permeability of the membrane (with or without opening). The membrane, which may be made of polycarbonate urethane, for example, dissolves in the body over time so that there is no further influence on the blood flow.

Detachable coupling elements for occlusion coils or stents are widely described in literature, especially those that are based on electrolytic, thermal or mechanical detachment techniques. Especially suited are electrolytic detachment systems in which an electrolytically corrodible part is dissolved by applying electrical energy resulting in the connection between the device and the insertion aid being severed. Suitable detachment elements are pre-corroded stainless steel elements, magnesium elements or cobalt-chromium alloys. Mechanical detachment techniques usually involve a form closure which is disengaged when the device is detached, so that the device becomes disconnected from the insertion aid.

The insertion wire may be of one-piece design, in which case the wire fundamentally has a continuous form. It is also possible, however, to combine the advantageous characteristics of different materials, for instance, the more proximally located part of the insertion wire can be made of stainless steel offering ease of forward movement, while the more distal part of the insertion wire can be made of a nickel-titanium alloy such as nitinol offering high flexibility. A distal section consisting of a nickel-titanium alloy also has the advantage that the risk of kinking is minimized ("kink resistance"). On the other hand, the use of a stiffer material such as stainless steel is advantageous for the proximal part of the insertion wire because it enables torque to be transmitted, which is advantageous in that it improves forward movement.

The term insertion aid is to be understood broadly and must not always refer to an insertion wire within the conventional sense of the word. For example, other elongated insertion aids having a hollow inner space may be employed as well.

As a rule, the inventive device has a length (without insertion aid) ranging between 5 mm and 40 mm and a diameter between 1.5 mm and 7 mm, the dimensions being determined by the dimension of the blood vessel from which the thrombus is to be eliminated. The figures indicated refer to the free, relaxed state of the device, that is, without the catheter exerting any external force. The struts forming the device may, for example, have a width, respectively diameter ranging between 20 and 60 μm.

Aside from the device itself the invention also relates to a method for producing the device. This is characterized by the fact that creating the constriction located between the middle and distal sections and causing the struts to be rounded off at the distal end of the distal section are brought about by a heat treatment.

Furthermore, the invention also relates to the use of the device proposed by the invention with a view to removing a thrombus from a blood vessel.

The invention is now described in detail by way of examples as follows with reference being made to the figures showing the respective embodiments. It is to be noted that the figures show preferred embodiment variants of the invention, but the invention shall not be deemed to be limited to these. To the extent it is technically expedient, the invention comprises, in general, any optional combinations of the technical features that are stated in the claims or in the description as being relevant to the invention.

BRIEF DESCRIPTION OF THE DRAWINGS

Elucidation of the invention is provided by the following figures where

FIG. 11a is a side view of the device according to the second embodiment shown with membrane after rounding of the distal end as a variant of FIG. 10a; and FIG. 11b is a frontal view of the device according to the second embodiment shown with membrane after rounding of the distal end as a variant of FIG. 10b.

DETAILED DESCRIPTION

Figure 1:
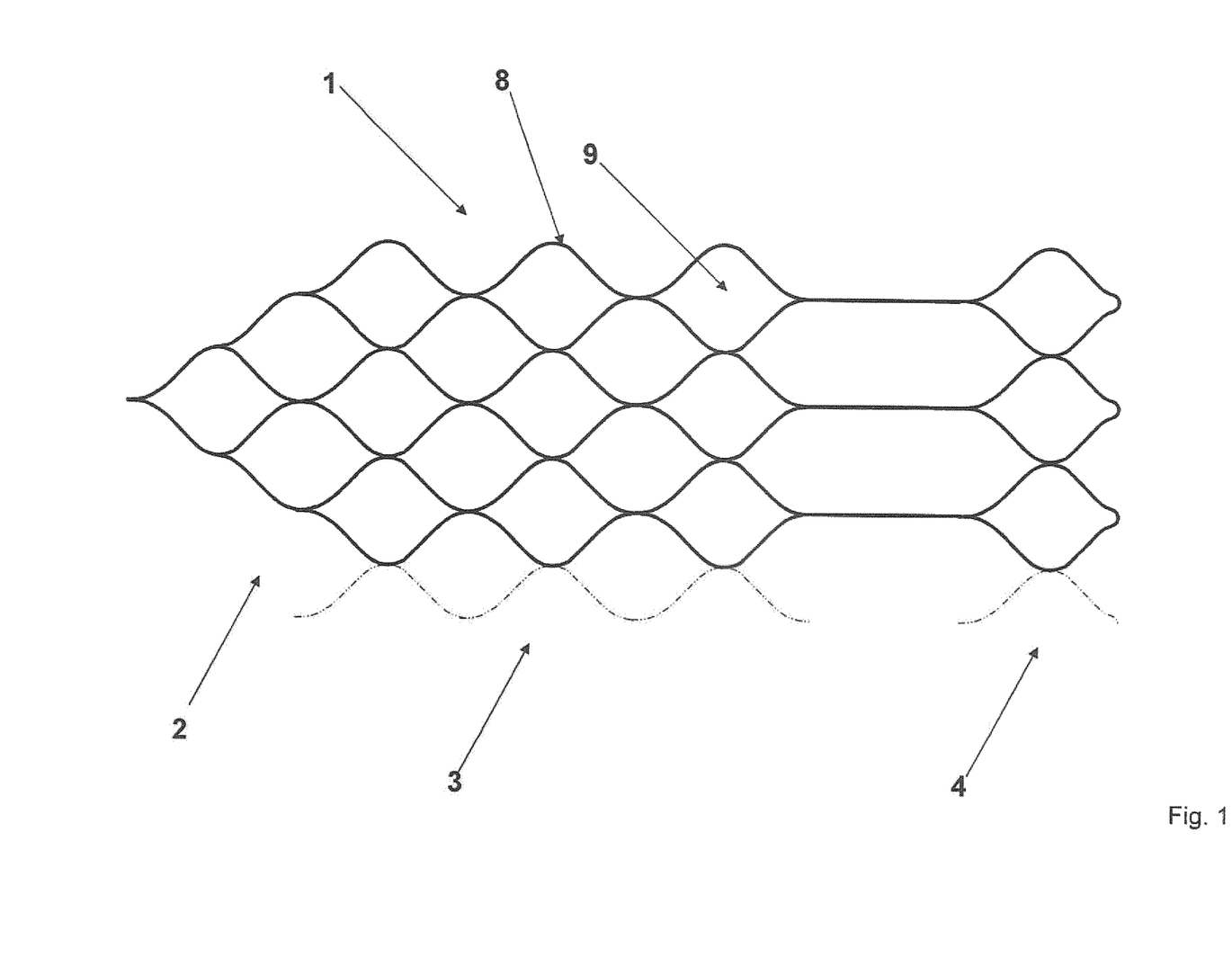
FIG. 1 shows the device according to a first variant of the first embodiment in rolled-out form without membrane.

In FIG. 1, the device 1 proposed by the invention is illustrated according to a first variant of the first embodiment, with the device 1 being shown in rolled-out form still without a membrane. It is in fact evident from the illustration that device 1 is essentially cylindrical in shape. Device 1 is provided with proximally located cross sectionally tapering and converging section 2, as well as with the middle, cylindrical section 3 and the distal section 4. It is made up of individual struts 8, which form open cells 9. In the present case, the number of open cells 9 arranged next to each other orthogonal to the longitudinal axis of device 1 is three. The dash-dotted lines indicate the connection to struts 8 on the opposite side of device 1.

Between middle section 3 and distal section 4 there is an area where device 1 exhibits fewer struts 8, said area being provided to enable a constriction to be formed during the process of bringing device 1 into a cylindrical shape.

Figure 2:
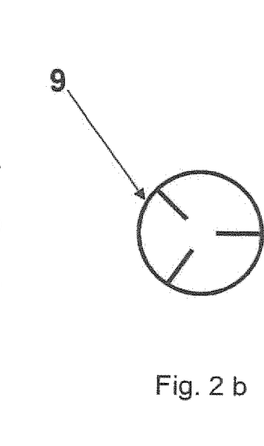
FIG. 2a is a side view of the device according to the first variant of the first embodiment shown without membrane.
FIG. 2b is a frontal view of the device according to the first variant of the first embodiment shown without membrane.

FIG. 2a illustrates the device shown in FIG. 1 in side view, but with a membrane not yet arranged. Moreover, the illustration of the individual open cells 9 was waived. Again, the proximal section 2, the middle section 3 and the distal section 4 can be seen, with constriction 6 being located between the middle section 3 and distal section 4, said constriction being produced by a heat treatment of the struts 8. At the proximal end, the device 1 terminates in a coupling point 11, by means of which it is attached to an insertion aid 5.

In FIG. 2b the device 1 shown in FIGS. 1 and 2a is illustrated in a frontal view, but again without the membrane that forms an inherent part of the invention. It can be seen that three open cells 9 each are arranged next to each other on the outer surface of device 1.

Figure 3:
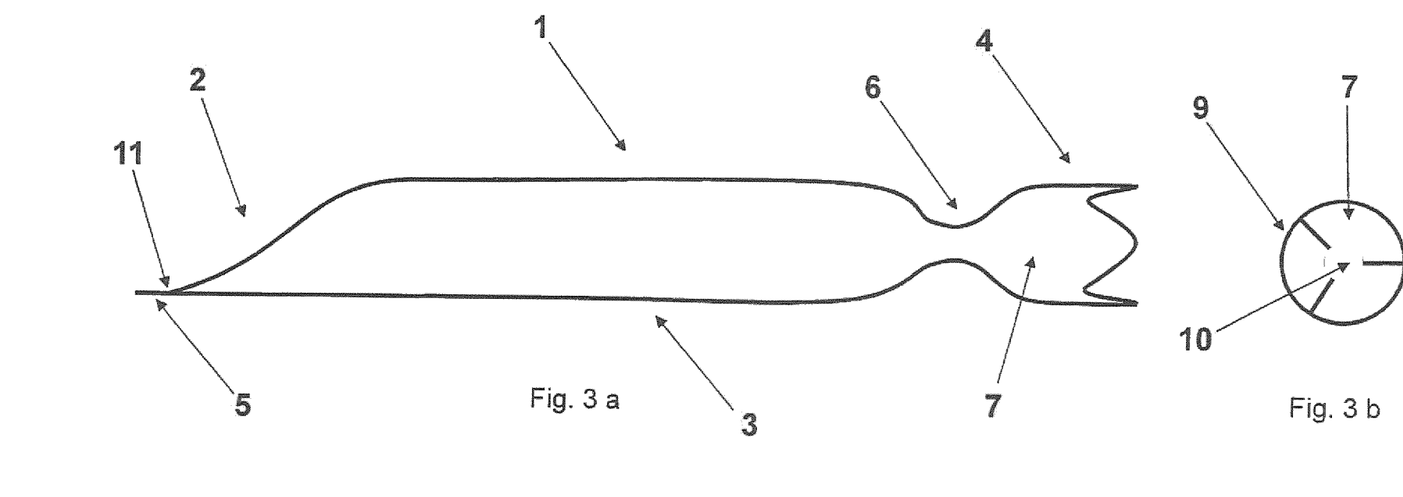
FIG. 3a is a side view of the device according to the first variant of the first embodiment shown with membrane.
FIG. 3b is a frontal view of the device according to the first variant of the first embodiment shown with membrane.

FIG. 3a corresponds to the illustration in FIG. 2a, however, after the device 1 has been provided with membrane 7. From the frontal view in FIG. 3b, it can be seen that membrane 7 has an opening 10 in the center, which serves the purpose of permanently maintaining the flow of blood.

Figure 4:
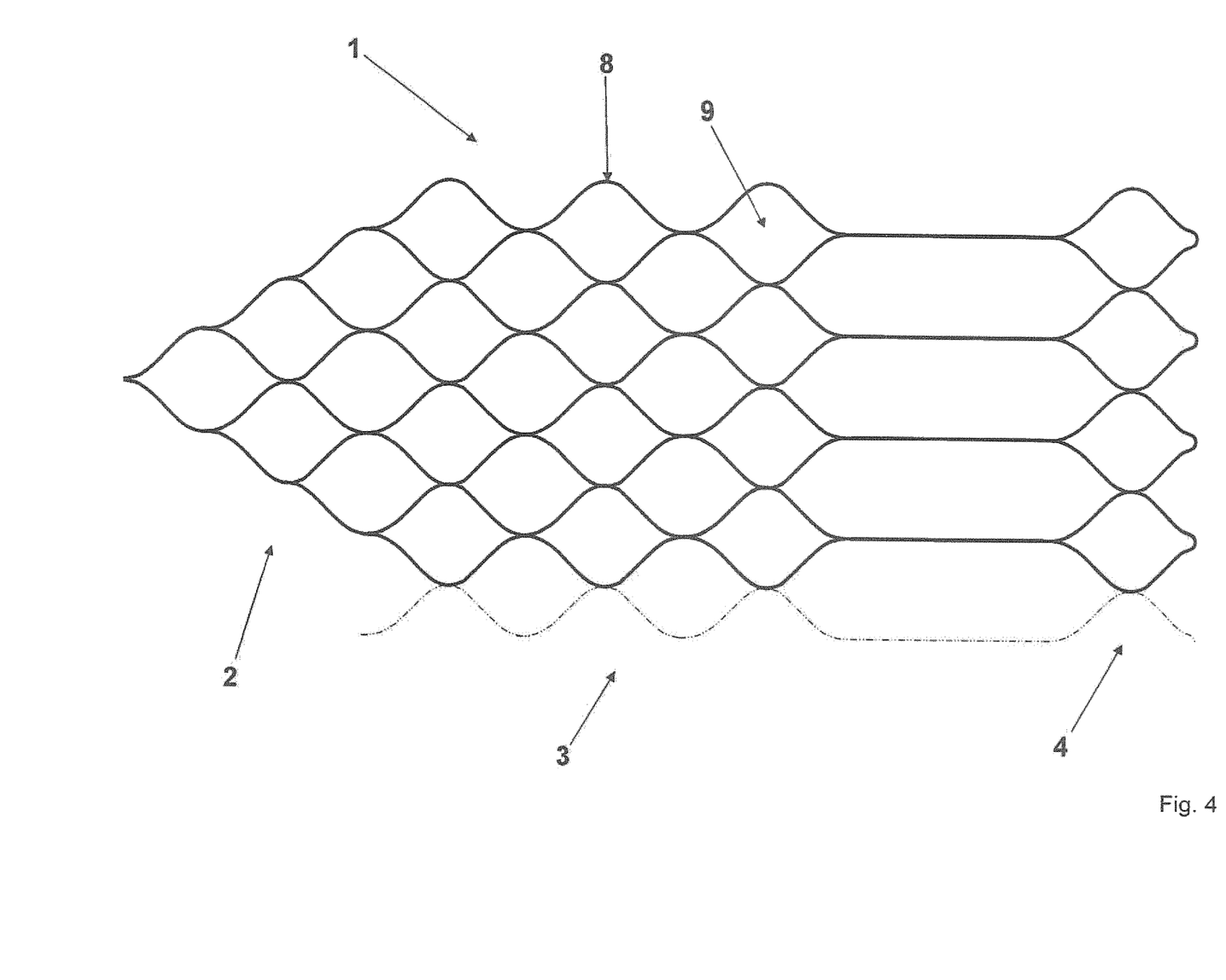
FIG. 4 shows the device according to a second variant of the first embodiment in rolled-out form without membrane.

In FIG. 4, a representation similar to that in FIG. 1 is chosen to provide a variant of device 1. Basically, FIG. 4 is similar to FIG. 1, however, the number of open cells 9 arranged next to each other is four in this case, with these cells 9 naturally being located radially side by side on the outer surface of the device 1 and form the cylindrical structure as a whole.

Figure 5:
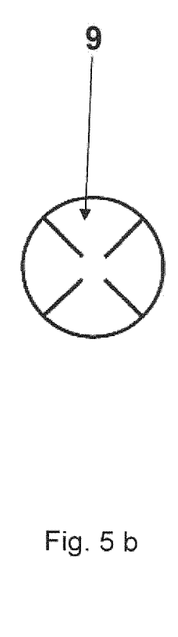
FIG. 5a is a side view of the device according to the second variant of the first embodiment shown without membrane.
FIG. 5b is a frontal view of the device according to the second variant of the first embodiment shown without membrane.

FIG. 5a illustrates in side view the variant as per FIG. 4, with a membrane not yet arranged. In contrast to FIG. 2a, the struts 8 are also shown here, which form the open cells 9. Again, the constriction 6 between the middle section 3 and the distal section 4 can be seen here.

FIG. 5b illustrates in frontal view the device shown in FIG. 5a, also without membrane. It is to be noted that the number of open cells 9 arranged next to each other on the outer surface, amounts to four.

Figure 6:
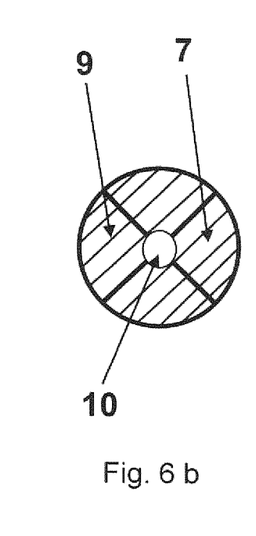
FIG. 6a is a side view of the device according to the second variant of the first embodiment shown with membrane.
FIG. 6b is a frontal view of the device according to the second variant of the first embodiment shown with membrane.

FIG. 6a depicts the embodiment shown in FIG. 5a, this time, however, after completion, i.e. including membrane 7. In the relevant frontal view of FIG. 6b it can be seen that the membrane 7 has a central opening 10.

Figure 7:
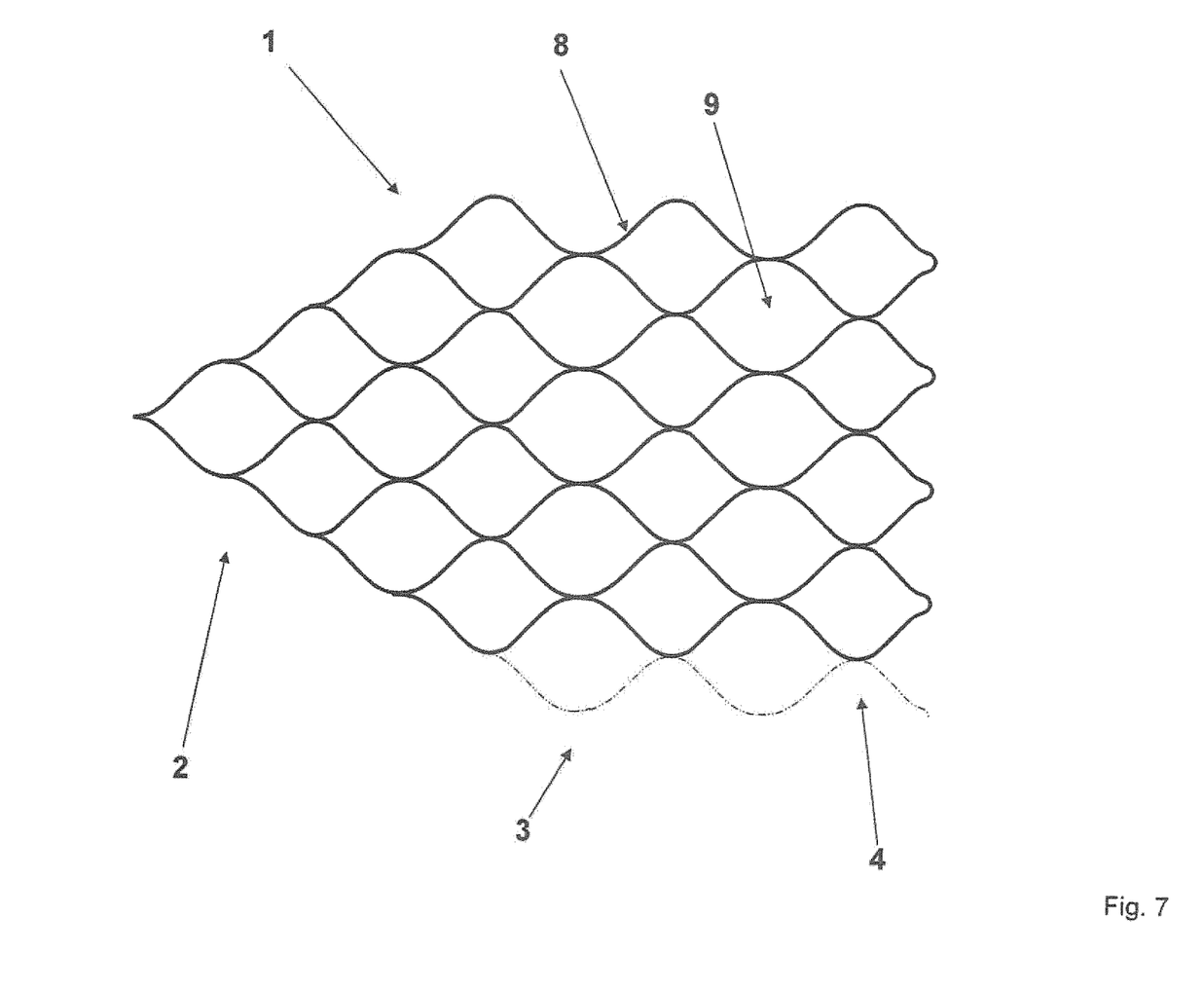
FIG. 7 shows the device according to a second embodiment in rolled-out form without membrane.

In FIG. 7, the second embodiment of device 1 is shown, still without a membrane, and with no constriction between the middle section 3 and distal section 4. FIG. 7 shows the rolled-out representation of device 1. The dash-dotted lines indicate that in reality the oppositely located open cells 9 follow here. Towards the proximal end, the proximal section 2 converges narrowly.

Figures 8, 9:
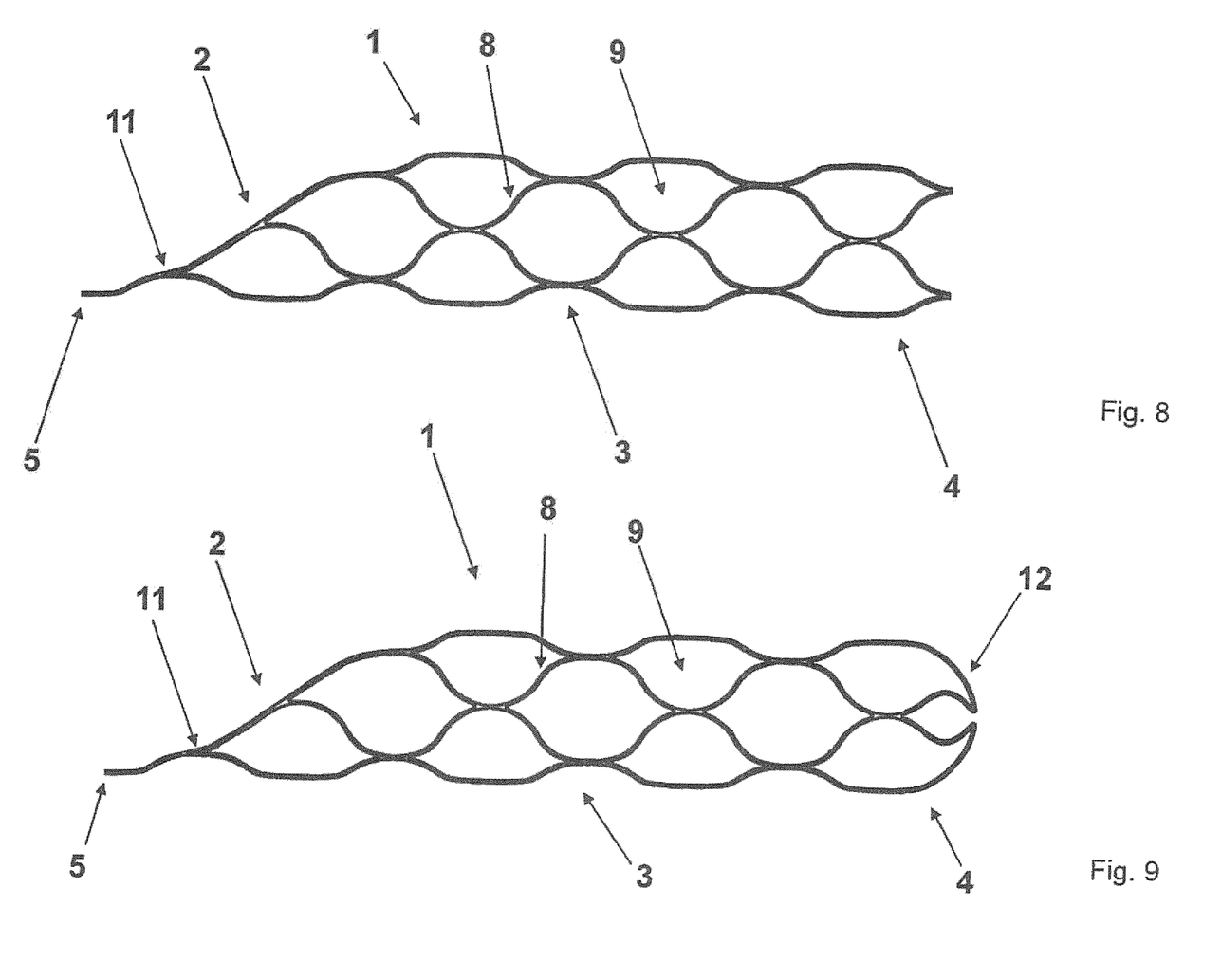
FIG. 8 is a side view of the device according to the second embodiment shown without membrane before rounding of the distal end.
FIG. 9 is a side view of the device according to the second embodiment shown without membrane after rounding of the distal end.

FIG. 8 illustrates the development process of the device according to the second embodiment of FIG. 7, with device 1 having already been formed into a cylindrical shape in FIG. 8. The struts 8 forming the open cells 9 ultimately converge in a coupling point 11 at the proximal section 2, with the device 1 being connected to the insertion aid 5 via this coupling point. It can be seen from FIG. 8 that the distal end in distal section 4 has not yet rounded.

The rounded configuration is shown in FIG. 9, i.e. here the struts 12 at the distal end of the distal section 4 are bent inwards, resulting in the distal section 4 having an overall curvature or bulging shape. The membrane 7 has not yet been arranged here.

Figure 10:
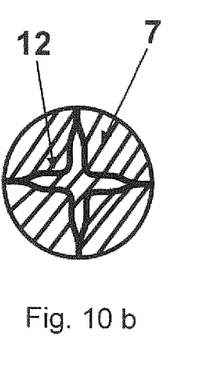
FIG. 10a is a side view of the device according to the second embodiment shown with membrane after rounding of the distal end.
FIG. 10b is a frontal view of the device according to the second embodiment shown with membrane after rounding of the distal end.

In conclusion, FIG. 10a shows in a side view the completed device 1 from FIGS. 7 to 9. The illustration differs from the presentation shown in FIG. 9 in that in this case the membrane was arranged in the distal section 4. The respective frontal view can be seen in FIG. 10b, which illustrates membrane 7 as well as the struts 12 which are bent inwards.

Figure 11:
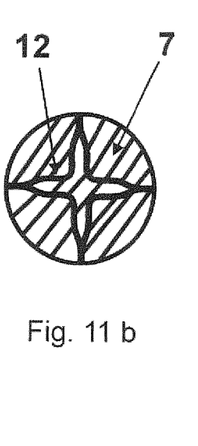

FIG. 11a is a variant of the device 1 shown in FIG. 10a, wherein the distal section 4 in which open cells 9 are covered by a membrane 7, extends further proximally. The frontal view 11b, on the other hand, does not differ from the variant shown in FIG. 10b.

The invention claimed is:

1. A device for removing thrombi from blood vessels, wherein the device has an expanded state in which it is set free temporarily in the blood vessel and a compressed state in which it is introduced into and removed from the blood vessel through a microcatheter, wherein the device has a proximal, a middle and a distal portion, with the middle portion having a substantially cylindrical structure and the proximal portion being coupled to an insertion aid wherein the distal portion has a substantially cylindrical basic structure and there is a constriction arranged between the middle and distal portion, and the distal portion being at least partially covered by a membrane, wherein the membrane has a funnel shape, with the thin end of the funnel pointing towards the constriction and the wide end pointing in the distal direction.

2. The device according to claim 1, wherein at least the middle section comprises a plurality of open cells distributed over its outer surface.

3. The device according to claim 2, wherein the number of open cells that are arranged adjacent to each other on the outer surface orthogonally to the longitudinal axis of the device is at least 2.

4. The device according to claim 3, wherein the number of open cells that are arranged adjacent to each other on the outer surface orthogonally to the longitudinal axis of the device is 3 to 5.

5. The device according to claim 1, wherein the membrane is provided with at least one opening.

6. The device according to claim 5, wherein the opening is centrally located in the membrane.

7. The device according to claim 1, wherein the insertion aid is coupled at one or several coupling points to the proximal portion of the device, wherein the coupling point is arranged radially displaced in the direction of the outer surface with respect to the centrally extending longitudinal axis of the device.

8. The device according to claim 1, with a slit which extends in the longitudinal direction of the device over the outer surface of at least a part of the device.

9. The device according to claim 8, wherein the slit extends parallel to the longitudinal axis of the device.

10. The device according to claim 8, wherein the slit extends helically over the outer surface.

11. The device according to claim 1, wherein at least some areas of the device are provided with a radiopaque coating.

12. A method for manufacturing a device according to claim 1, wherein creating a constriction between the middle and the distal portion is brought about by means of a heat treatment.

* * * * *